United States Patent
Parel et al.

(10) Patent No.: US 9,974,646 B2
(45) Date of Patent: May 22, 2018

(54) KERATOPROSTHESIS, AND SYSTEM AND METHOD OF CORNEAL REPAIR USING SAME

(71) Applicant: UNIVERSITY OF MIAMI, Miami, FL (US)

(72) Inventors: Jean-Marie Parel, Miami Shores, FL (US); Yoh Sawatari, Coral Gables, FL (US); Victor L. Perez, Miami, FL (US); Andres Bernal, Sunny Isles Beach, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 0 days. days.

(21) Appl. No.: 14/426,195

(22) PCT Filed: Sep. 4, 2013

(86) PCT No.: PCT/US2013/057949
§ 371 (c)(1),
(2) Date: Mar. 5, 2015

(87) PCT Pub. No.: WO2014/039495
PCT Pub. Date: Mar. 13, 2014

(65) Prior Publication Data
US 2015/0216651 A1    Aug. 6, 2015

Related U.S. Application Data

(60) Provisional application No. 60/696,937, filed on Sep. 5, 2012.

(51) Int. Cl.
*A61F 2/14*    (2006.01)

(52) U.S. Cl.
CPC .................................. *A61F 2/142* (2013.01)

(58) Field of Classification Search
CPC .......... A61F 2/142; A61F 2/145; A61F 2/147; A61F 2/16; A61L 27/16
See application file for complete search history.

(56) References Cited

U.S. PATENT DOCUMENTS

| | | | |
|---|---|---|---|
| 2,517,523 A | 8/1950 | Batchelder | |
| 2,714,721 A | 8/1955 | Stone, Jr. | |
| (Continued) | | | |

FOREIGN PATENT DOCUMENTS

| | | |
|---|---|---|
| AU | 650156 | 10/1994 |
| BG | 107181 | 4/2004 |
| (Continued) | | |

OTHER PUBLICATIONS

Linnola, Titanium and bioactive glass-ceramic coated titanium as materials for keratoprosthesis, Experimental Eye Research. (63(4):471-8, 119 Oct. (Abstract).*

(Continued)

*Primary Examiner* — David H Willse
*Assistant Examiner* — Tiffany Shipmon
(74) *Attorney, Agent, or Firm* — Marshall, Gerstein & Borun LLP

(57) ABSTRACT

A keratoprosthesis and system and method of using same for corneal repair. The keratoprosthesis comprises a biocompatible support and an optic member disposed through a channel within the support. The support includes metal, preferably titanium, and treated, such as by sandblasting and/or acid etching, to create textured surfaces that promote soft tissue adhesion. A locking member interconnects the optic member and support. An outer surface of the locking member a collar extending from the support and disposed around the optic member is also metal, preferably titanium, and is similarly treated to promote soft tissue adhesion. A locking member interconnects the optic member and sup- (Continued)

port. The system includes the keratoprosthesis positioned within an isolated soft tissue segment of a non-ocular tissue, such as buccal mucosa, placed on the anterior cornea. The method includes removing corneal epithelium, isolating and transplanting a segment of soft tissue to the de-epithelialized cornea, creating a receiving area in the soft tissue, positioning a keratoprosthesis relative to the receiving area anterior to the cornea, and securing the keratoprosthesis.

29 Claims, 10 Drawing Sheets

(56) References Cited

U.S. PATENT DOCUMENTS

| | | |
|---|---|---|
| 2,754,520 A | 7/1956 | Crawford, Jr. |
| 2,952,023 A | 9/1960 | Rosen |
| 3,074,407 A | 1/1963 | Moon |
| 3,454,966 A | 7/1969 | Rosen |
| 3,458,870 A | 8/1969 | Stone, Jr. |
| 3,945,054 A * | 3/1976 | Fedorov .................. A61F 2/142 623/5.14 |
| 3,992,563 A | 11/1976 | Tanaka |
| 4,223,984 A | 9/1980 | Miyata et al. |
| 4,285,073 A | 8/1981 | Szycher |
| 4,396,039 A | 8/1983 | Klenk et al. |
| 4,424,335 A | 1/1984 | Szycher |
| 4,470,159 A | 9/1984 | Peyman |
| 4,500,382 A | 2/1985 | Foster |
| 4,505,855 A | 3/1985 | Bruns et al. |
| 4,563,779 A | 1/1986 | Kelman |
| 4,581,030 A | 4/1986 | Bruns et al. |
| 4,586,929 A | 5/1986 | Binder |
| 4,607,617 A | 8/1986 | Choyce |
| 4,612,012 A | 9/1986 | White |
| 4,618,649 A | 10/1986 | Ofstead |
| 4,624,669 A | 11/1986 | Grendahl |
| 4,676,790 A | 6/1987 | Kern |
| 4,693,715 A | 9/1987 | Abel, Jr. |
| 4,693,939 A | 9/1987 | Ofstead |
| 4,715,858 A | 12/1987 | Lindstrom |
| 4,772,283 A | 9/1988 | White |
| 4,786,446 A | 11/1988 | Hammar et al. |
| 4,799,931 A | 1/1989 | Lindstrom |
| 4,810,082 A | 3/1989 | Abel, Jr. |
| 4,840,992 A | 6/1989 | Ofstead |
| 4,842,599 A | 6/1989 | Bronstein |
| 4,851,003 A | 7/1989 | Lindstrom |
| 4,865,601 A | 9/1989 | Caldwell |
| 4,883,864 A | 11/1989 | Scholz |
| 4,921,908 A | 5/1990 | Ofstead |
| 4,923,466 A | 5/1990 | Pintucci |
| 4,976,732 A | 12/1990 | Vorosmarthy |
| 4,994,081 A | 2/1991 | Civerchia et al. |
| 5,019,097 A | 5/1991 | Knight et al. |
| 5,024,742 A | 6/1991 | Nesburn et al. |
| 5,030,230 A | 7/1991 | White |
| 5,044,743 A | 9/1991 | Ting |
| 5,067,961 A | 11/1991 | Kelman et al. |
| 5,108,428 A | 4/1992 | Capecchi et al. |
| 5,112,350 A | 5/1992 | Civerchia et al. |
| 5,123,921 A | 6/1992 | Werblin et al. |
| 5,139,518 A | 8/1992 | White |
| 5,152,788 A | 10/1992 | Isaacson et al. |
| 5,171,318 A | 12/1992 | Gibson et al. |
| 5,196,026 A | 3/1993 | Barrett et al. |
| 5,215,104 A | 6/1993 | Steinert |
| 5,292,514 A | 3/1994 | Capecchi et al. |
| 5,294,314 A | 3/1994 | Nesburn et al. |
| 5,300,115 A | 4/1994 | Py |
| 5,300,116 A | 4/1994 | Chirila et al. |
| 5,332,802 A | 7/1994 | Kelman et al. |
| 5,336,261 A | 8/1994 | Barrett et al. |
| 5,354,332 A | 10/1994 | Lacombe |
| 5,366,499 A | 11/1994 | Py |
| 5,387,106 A | 2/1995 | MacKenzie et al. |
| 5,391,201 A | 2/1995 | Barrett et al. |
| 5,401,508 A | 3/1995 | Manesis |
| 5,431,790 A | 7/1995 | Nesburn et al. |
| 5,433,745 A | 7/1995 | Graham et al. |
| 5,443,473 A | 8/1995 | Miller et al. |
| 5,458,819 A | 10/1995 | Chirila et al. |
| 5,489,300 A | 2/1996 | Capecchi et al. |
| 5,489,301 A | 2/1996 | Barber |
| 5,628,794 A | 5/1997 | Lindstrom |
| 5,632,773 A | 5/1997 | Graham et al. |
| 5,652,640 A | 7/1997 | Schneider et al. |
| 5,660,692 A | 8/1997 | Nesburn et al. |
| 5,693,095 A | 12/1997 | Freeman et al. |
| 5,713,956 A | 2/1998 | Legeals |
| 5,713,957 A | 2/1998 | Steele et al. |
| 5,743,868 A | 4/1998 | Brown et al. |
| 5,744,515 A | 4/1998 | Clapper |
| 5,822,091 A | 10/1998 | Baker |
| 5,836,313 A | 11/1998 | Perez et al. |
| 5,843,185 A * | 12/1998 | Leon Rolden .......... A61F 2/142 623/5.11 |
| 5,945,498 A | 8/1999 | Hopken et al. |
| 5,962,005 A | 10/1999 | Saga et al. |
| 5,973,089 A | 10/1999 | Meijs et al. |
| 6,005,160 A | 12/1999 | Hsiue et al. |
| 6,036,891 A | 3/2000 | Liao et al. |
| 6,043,328 A | 3/2000 | Domschke et al. |
| 6,090,141 A | 7/2000 | Lindstrom |
| 6,102,946 A | 8/2000 | Nigam |
| 6,106,552 A | 8/2000 | Lacombe et al. |
| 6,210,005 B1 | 4/2001 | Portney |
| 6,254,637 B1 * | 7/2001 | Lee ........................ A61F 2/142 128/898 |
| 6,271,332 B1 | 8/2001 | Lohmann et al. |
| 6,346,121 B1 | 2/2002 | Hicks |
| 6,361,560 B1 | 3/2002 | Nigan |
| 6,391,055 B1 | 5/2002 | Ikada et al. |
| 6,423,093 B1 | 7/2002 | Hicks |
| 6,436,481 B1 | 8/2002 | Chabrecek et al. |
| 6,440,167 B2 | 8/2002 | Shimizu |
| 6,444,776 B1 | 9/2002 | Holland et al. |
| 6,447,118 B1 | 9/2002 | Okumura et al. |
| 6,447,920 B1 | 9/2002 | Chabrecek et al. |
| 6,454,800 B2 | 9/2002 | Dalton et al. |
| 6,468,667 B1 | 10/2002 | Chabrecek et al. |
| 6,472,489 B1 | 10/2002 | Stockinger |
| 6,503,958 B2 | 1/2003 | Hughes et al. |
| 6,521,352 B1 | 2/2003 | Chabrecek et al. |
| 6,533,415 B2 | 3/2003 | Watanabe |
| 6,537,569 B2 | 3/2003 | Cruise |
| 6,537,808 B2 | 3/2003 | Lambiase |
| 6,544,286 B1 | 4/2003 | Perez |
| 6,555,103 B2 | 4/2003 | Leukel et al. |
| 6,582,754 B1 | 6/2003 | Pasic et al. |
| 6,586,038 B1 | 7/2003 | Chabrecek et al. |
| 6,589,665 B2 | 7/2003 | Chabrecek et al. |
| 6,592,621 B1 | 7/2003 | Domino |
| 6,595,639 B1 | 7/2003 | Ho et al. |
| 6,605,093 B1 | 8/2003 | Blake |
| 6,607,556 B1 | 8/2003 | Nigam |
| 6,609,793 B2 | 8/2003 | Norrby et al. |
| 6,626,941 B2 | 9/2003 | Nigam |
| 6,631,562 B1 | 10/2003 | Balzer et al. |
| 6,632,244 B1 | 10/2003 | Nigam |
| 6,638,991 B2 | 10/2003 | Baba et al. |
| 6,645,715 B1 | 11/2003 | Griffith et al. |
| 6,653,420 B2 | 11/2003 | Domschke et al. |
| 6,663,668 B1 | 12/2003 | Chaouk et al. |
| 6,673,112 B2 | 1/2004 | Nigam |
| 6,679,605 B2 | 1/2004 | Zhou et al. |
| 6,686,437 B2 | 2/2004 | Buchman et al. |
| 6,689,165 B2 | 2/2004 | Jacob et al. |
| 6,702,983 B2 | 3/2004 | Hu et al. |
| 6,706,036 B2 | 3/2004 | Lai |
| 6,713,524 B2 | 3/2004 | Leukel et al. |
| 6,719,929 B2 | 4/2004 | Winterton et al. |
| 6,730,366 B2 | 5/2004 | Lohmann et al. |

(56) References Cited

U.S. PATENT DOCUMENTS

| | | | |
|---|---|---|---|
| 6,733,526 B2 | 5/2004 | Paul et al. | |
| 6,734,281 B2 | 5/2004 | Hopken et al. | |
| 6,734,321 B2 | 5/2004 | Chabrecek et al. | |
| 6,755,858 B1 | 6/2004 | White | |
| 6,770,728 B2 | 8/2004 | Watanabe et al. | |
| 6,780,899 B2 | 8/2004 | Liao et al. | |
| 6,780,930 B2 | 8/2004 | Lewis et al. | |
| 6,811,805 B2 | 11/2004 | Gilliard et al. | |
| 6,814,755 B2 | 11/2004 | Lacombe et al. | |
| 6,827,885 B2 | 12/2004 | Altmann et al. | |
| 6,827,966 B2 | 12/2004 | Qiu et al. | |
| 6,835,410 B2 | 12/2004 | Chabrecek et al. | |
| 6,846,897 B2 | 1/2005 | Salamone et al. | |
| 6,849,210 B2 | 2/2005 | Bothe et al. | |
| 8,506,626 B2 | 8/2013 | Azar et al. | |
| 2002/0010510 A1 | 1/2002 | Silvestrini | |
| 2003/0033010 A1 | 2/2003 | Hicks et al. | |
| 2003/0055497 A1 | 3/2003 | Hicks et al. | |
| 2008/0221676 A1 | 9/2008 | Coleman et al. | |
| 2008/0255663 A1 | 10/2008 | Akpek et al. | |
| 2010/0069915 A1 | 3/2010 | Shiuey | |
| 2010/0168849 A1 | 7/2010 | Azar et al. | |
| 2011/0160851 A1* | 6/2011 | Mueller-Lierheim | A61F 2/142 623/5.13 |

FOREIGN PATENT DOCUMENTS

| | | | |
|---|---|---|---|
| CN | 1266669 | * | 9/2000 |
| EP | 956834 A2 | | 11/1999 |
| EP | 1408881 | | 4/2004 |
| EP | 1289451 B1 | | 12/2004 |
| FR | 2649605 | * | 1/1991 |
| GB | 2403908 A | | 1/2005 |
| RU | 2120307 | | 8/1995 |
| RU | 2124331 C1 | | 3/1997 |
| RU | 2102939 C1 | | 1/1998 |
| RU | 2139014 | * | 10/1999 |
| RU | 2139014 C1 | | 10/1999 |
| RU | 2150956 C1 | | 6/2000 |
| RU | 2157147 | * | 10/2000 |
| RU | 2157147 C1 | | 10/2000 |
| RU | 2162678 C1 | | 2/2001 |
| RU | 2179427 C2 | | 2/2002 |
| SU | 1734725 | * | 1/1990 |
| WO | WO02089709 A1 | | 11/2002 |
| WO | WO2004028410 A1 | | 4/2004 |
| WO | WO2014039495 A1 | | 3/2014 |

OTHER PUBLICATIONS

KPRO Study Group Bibliography of Keratoprosthesis and Artificial Corea and Biomaterials Therefor from 1789 to 2015; Compiled at the Bascom Palmer Eye Institute under the Guidance of the KPRO Steering Committee, Last Update Mar. 23, 2015.

* cited by examiner

KERATOPROSTHESIS, AND SYSTEM AND METHOD OF CORNEAL REPAIR USING SAME

CLAIM OF PRIORITY

The present application is based on and a claim of priority is made under 35 U.S.C. Section 119(e) to a provisional patent application that is currently pending in the U.S. Patent and Trademark Office, namely, that having Ser. No. 60/696,937 and a filing date of Sep. 5, 2012, and which is incorporated herein by reference.

STATEMENT OF GOVERNMENT SUPPORT

This invention was made with government support under grant number W81XWH-09-1-0674 awarded by USARMY MEDCOM USAMRAA. The government has certain rights in the invention

BACKGROUND OF THE INVENTION

1. Field of the Invention

The present invention relates to corneal repair, and more in particular, to a novel keratoprosthesis that provides enhanced soft tissue adhesion and less extrusion, a system for repairing severely damaged cornea using such keratoprosthesis, and a method of implanting such keratoprosthesis to effect corneal repair.

2. Description of the Related Art

One of the greatest challenges in ophthalmology is the management of the severely damaged cornea. Severe damage to the cornea can arise from Stevens Johnson's syndrome, chemical burns, Cicatricial pemphigoid, Lyell's syndrome and recurrent graft failure, for example. These conditions can lead to scarring of the cornea and corneal blindness that is not amenable to treatment or repair by common techniques such as corneal transplantation (also called "penetrating keratoplasty"). In these circumstances, management is limited to a keratoprosthesis.

The three most frequently used keratoprostheses currently are the autogenous modified osteo-odonto keratoprosthesis (MOOKP), the alloplastic Boston Keratoprosthesis®, and the AlphaCor™ keratoprosthesis. The Alphacor™ keratoprosthesis was abandoned in the United States due to poor results after two years, mainly caused by retraction of the cornea at the interface with the prosthesis which can cause aqueous leaks and consequent loss of intraocular pressure and potential endophthalmitis. The Boston Keratoprosthesis® has had better results but also suffers from cornea thinning and retraction at the cornea-implant interface which, if not repaired in time, can also lead to extrusion, or rejection of the implant, and endophthalmitis. Also, the Boston Keratoprosthesis® requires a donor cornea. Human tissue availability might be problematic in countries where donor tissue is difficult to obtain or not available. In addition, as the Boston Keratoprosthesis® has a fixation member, a plastic or a metal ring, located in the anterior chamber of the patient, contact with the iris is problematic as when the patient's iris closes in bright light, it may contact the fixation ring or the protruding posterior surface of the implant and iris inflammation occurs. The inflammation can induce fibrinous secretion which engenders the formation of an opaque intraocular fibrous capsule (called retroprosthetic membrane) which impedes vision and needs intraocular surgery to be resected. The fibrous membrane sometimes closes the anterior chamber angle preventing normal aqueous outflow and the intraocular pressure rises. If the membrane is not removed surgically, the increase in intraocular pressure may cause glaucoma and loss of vision. The major problem with all alloplastic keratoprostheses is the lack of tissue attachment, and therefore a potential rejection.

Of the current keratoprostheses, the MOOKP has had the most success thus far, having been used for over 30 years with a documented success rate of approximately 85%. Generally, the MOOKP comprises a polymethylmethacrylate (PMMA) optic cylinder embedded into an autogenous graft consisting of tooth, periodontal ligament (PDL), bone, and periosteum. The implantation procedure is a multistep process involving both maxillofacial and ocular surgery. The first step includes preparing the eye by cutting and removing the synechiaes to free the globe, removing all corneal and conjunctival epithelium, and removing the crystalline lens and iris. The second step includes the excision and transfer of oral buccal mucosa from the patient's mouth to the anterior surface of the eye. A combination of tooth and bone is then resected from the patient and formed into a support skirt of approximately 3 millimeters in thickness. The selection of a tooth used in the MOOKP procedure is based on clinical and radiographic evaluation of the patient's dentition. The surgeon selects the largest tooth root, usually the maxillary canine, for use in the MOOKP. The largest root allows for the optical cylinder with the largest diameter to be utilized for the prosthesis. Traditionally, the optical cylinder varies in diameter between three and four millimeters. The larger the cylinder, the wider the field of view for the patient, therefore the largest optical cylinder (determined by the width of the patient's chosen canine, which varies patient-to-patient) that can be fitted into the support skirt, or lamina, without causing structural damage is selected. A hole is then hand-drilled in the support skirt to fit the selected optical cylinder, which is then cemented into the skirt to form the MOOKP. The skirt is then implanted into a subcutaneous pocket within the cheek or subclavicular chest wall of the patient. After a three month healing period, which allows the formation of a neovascular network of tissue and blood vessels to attach to the prosthesis, the third step of the procedure involves transplanting the prosthesis, along with the newly attached tissue, from the subcutaneous pocket to a pocket created deep to the transplanted buccal mucosa over the host cornea. The de novo tissues attached to the implant are then sutured to the surrounding environment to keep the prosthesis in place.

Despite its relative success, the MOOKP suffers from multiple complications and drawbacks. For example, ocular complications can develop subsequent to implantation, including glaucoma, infection, extrusion, and retinitis. In fact, a primary cause of keratoprosthesis failure is extrusion, in which epithelial cells infiltrate the implant area and literally push the implant out. Secondary infections resulting from bacterial invasion upon epithelial infiltration is also a major problem contributing to prosthesis rejection. Dental complications arising from the resection of the osteo-odonto lamina may produce damage to adjacent teeth, oro-nasal and oro-antral communication, infection, sinusitis, and nerve damage. Drawbacks of the MOOKP procedure include a poor cosmetic outcome of the eye. Although a shell can be developed to cover the buccal mucosa in an attempt to improve the cosmesis of the eye, often times the osteo-odonto lamina or skirt displaces such a large volume of space that the eye cannot be appropriately covered. Therefore, the appearance of the eye cannot be fully or completely improved. In another drawback, the MOOKP procedure creates a surgical defect of the oral cavity from the removal of tooth and bone. This defect ideally can be reconstructed utilizing a bone graft followed by a dental implant or additional options of dental rehabilitation. However, such an oral defect is complex and generally is difficult to reconstruct. Finally, the multistage nature of the MOOKP procedure, involving two different groups of surgeons, and the duration of the various steps makes it an inherently prolonged procedure with numerous opportunities for complications to arise.

A new keratoprosthesis is therefore needed which emulates the success of the MOOKP without the resultant complications and defects. The ideal keratoprosthesis should have optimal biointegration, resist infection, replicate qualities of the cornea including drug penetration and intraocular pressure measurements, and last the lifetime of the patient. The keratoprosthesis should also prevent, or at least reduce, the risk of extrusion and rejection of the keratoprosthesis as well as iris inflammation.

SUMMARY OF THE INVENTION

The present invention is directed to a novel keratoprosthesis and a system and method for implementing the same in repairing severe corneal damage. The keratoprosthesis comprises a support made of a biocompatible material, preferably titanium, and is disposable fully anterior of the cornea of an eye within a pocket of non-ocular tissue placed thereon. Moreover, the present invention enables improved soft tissue adhesion, which results in less extrusion, than previously known keratoprostheses for treating severely damaged cornea. It also obviates many of the complications and drawbacks of known keratoprostheses. For instance, use of the present keratoprosthesis presents no oral defects.

More in particular, the keratoprosthesis of the present invention comprises a support, also termed a skirt, which may be made entirely of titanium or of a laminate or composite having outer surfaces of titanium. An optic member is disposed through the support in vision facilitating relation to the eye. The support also includes a plurality of apertures located along the periphery of the support to facilitate securing of the keratoprosthesis in position upon implantation. The support may also comprise a plurality of openings disposed throughout the support, which may be contoured, to allow for tissue integration as well as nutrients and hydration to permeate the keratoprosthesis for overall eye health and prolonged successful implantation.

A collar extends from the support and surrounds the optic member such that any surface of the keratoprosthesis that comes into contact with the surrounding environment is titanium. These titanium surfaces are pre-treated to create a microstructure that promotes the adhesion of the surrounding soft tissue thereto which forms a bioseal with the keratoprosthesis, preventing epithelial encroachment and resulting extrusion. For example, the titanium surface may be pre-treated with sandblasting and/or acid etching to produce texture on the surface to which the soft tissue may attach and adhere. A locking member may also be disposed between the optic member and collar to secure the optic member to the titanium support.

The present invention is also directed to a system for corneal repair including the above-described keratoprosthesis and an isolated soft tissue segment of non-ocular tissue disposed on the surface of a cornea from which the damaged portion or corneal epithelium has been removed. In one embodiment, the non-ocular tissue is oral mucosa, such as buccal mucosa, taken from the inner cheek of a patient. In the present system, the keratoprosthesis is placed within the isolated soft tissue anterior to the cornea, and in at least one embodiment, in substantially isolated relation from the cornea such that the support of the keratoprosthesis does not contact the cornea.

The present invention is further directed to a method of implanting the above-described keratoprosthesis. This method involves removing a portion of corneal epithelium from a damaged cornea, creating a de-epithelialized section of cornea. A segment of soft tissue is isolated, such as from the cheek of a patient or other non-ocular donor site, and the isolated soft tissue segment is positioned on the de-epithelialized section of cornea and may be allowed to graft thereto. A receiving area within the soft tissue segment is created, such as by making an incision or pocket. The keratoprosthesis is inserted into the receiving area of the soft tissue so that the keratoprosthesis is located entirely anterior to the cornea, and preferably not in contact with the cornea. The keratoprosthesis is then secured in place within the soft tissue segment, such as by suturing the support of the keratoprosthesis to the surrounding soft tissue and/or cornea.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION

Figure 1:
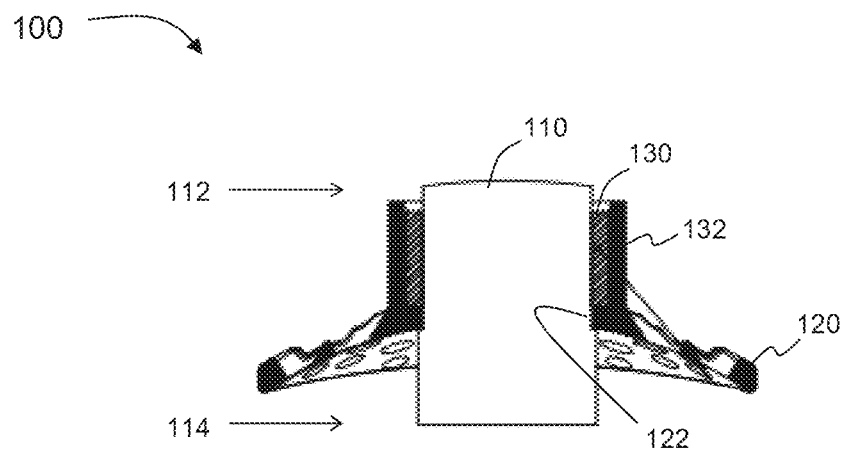
FIG. 1 is a cut away side view of one embodiment of a keratoprosthesis of the present invention.

The present invention is directed to a novel keratoprosthesis and a system and method for implementing the same in repairing severe corneal damage. The present invention promotes the adhesion of soft tissue to the implanted keratoprosthesis to form a bioseal, prohibiting epithelial infiltration and extrusion that plagues currently available keratoprostheses. Moreover, the present keratoprosthesis produces no oral defects, and involves fewer ocular complications.

To begin, the keratoprosthesis of the present invention, shown throughout the Figures as 100, comprises an optic member 110 disposable in vision facilitating relation to the eye of a patient. As should be readily understood by those skilled in the art, the optic member is a cylinder or tube-like structure that houses a lens through which light passes in order for vision to occur. The optic member 110 used herein may be made from any appropriate and biologically compatible material, such as polymethylmethacrylate (PMMA), polysulfone, trimethyl terminated polydimethylsiloxane (PDMS), polysterene-polyisobutylene-polysterene (SIBS) etc. The optic member 110 may be any size sufficient to accommodate vision, such as to permit an appropriate amount of light to pass through. In at least one embodiment the optic member 110 has a diameter of approximately 4 millimeters.

The keratoprosthesis 100 further includes a biocompatible support 120, which may also be referred to as a skirt or lamina of the keratoprosthesis. The support 120 is made of a biocompatible material that is biologically inert and will not react or cause a reaction in the body. In at least one embodiment, the support 120 is made of a metallic material. This is in contrast to known keratoprostheses, which typically employ a bone complex or PMMA for the skirt. However, all corneal cells have shown some form of reaction to PMMA, such as neovascularization, necrosis, and corneal melting, all of which predispose the prosthesis to extrusion and failure. The present keratoprosthesis 100, on the other hand, utilizes an alloplastic and biologically inert material, such as a metal, thereby avoiding such problems.

In a preferred embodiment, the support 120 comprises titanium. Titanium is an inert metal having high biocompatibility that has been successfully used in other medical implantation procedures. In addition to biocompatibility, titanium has additional characteristics that make it amenable for use in implantation, including rigidity, lack of evoking an inflammatory response, resistance to corrosion, and integration with bone and soft tissue.

In at least one embodiment, the support 120 is made entirely of titanium, such as milled from a single piece of titanium. In other embodiments, the support 120 is made of a core of biocompatible material and has an outer surface of titanium. For instance, the core may be made of a laminate or composite of materials, which may be rigid or flexible. In some embodiments, the core may be made of films or layers of material bonded together. Examples of core material include, but are not limited to, polymeric materials such as polychlorotrifluoroethylene, metals such as stainless steel, and/or combinations thereof. At least one surface of the support 120 comprises titanium, and preferably the entire outer surface of the support 120 comprises titanium. For instance, the surfaces of the core can be impregnated or loaded with a titanium-containing material, such as titanium powder. In another embodiment, the core is coated with titanium, such as by any of various deposition techniques, including but not limited to surface or particle deposition through the use of plasma or other techniques, or any other method of permanently adhering titanium to the surface of the core.

Figure 2:
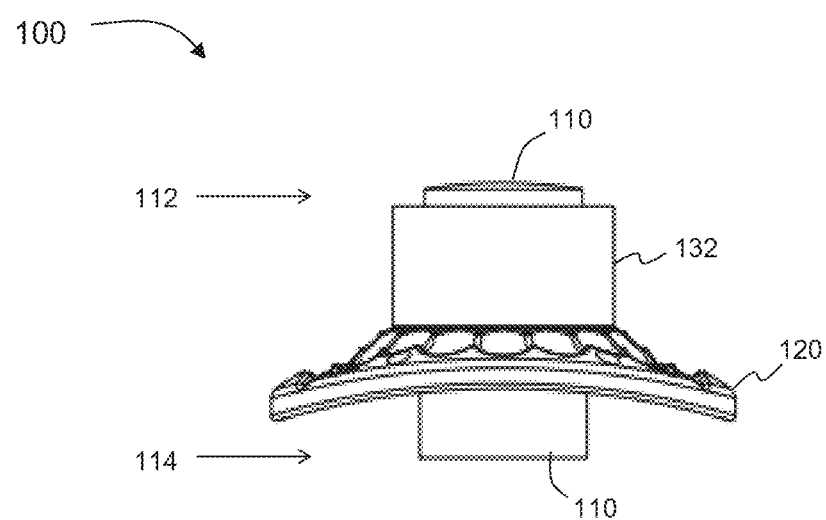
FIG. 2 is a side elevation of the keratoprosthesis of FIG. 1.

The support 120 is sufficiently shaped to stably support the keratoprosthesis 100 upon implantation. For example, the support 120 may have an extended length, and may comprise an elliptical discoid shape. In some other embodiments, the support 120 comprises a more circular shape. The diameter of the support 120 is appropriately sized to correspond to the size of the cornea, though it may be smaller or larger in diameter than a cornea. For instance, the diameter of the support 120 may be in the range of about 5 to 14 millimeters. In at least one embodiment, the diameter is approximately 8 millimeters. In another embodiment, the diameter is approximately 10 millimeters. In at least one other embodiment, in which the support 120 comprises an elliptical shape, the diameter of the support 120 is 10 millimeters along the long axis and 8 millimeters along the short axis (10 mm×8 mm). Moreover, the support 120 is relatively thin, having a thickness of less than 1 millimeter in at least one embodiment. As best shown in FIGS. 1 and 2, the support 120 also comprises an appropriate curvature that corresponds to the curvature of the cornea of a patient.

As shown in FIG. 1, the biocompatible support 120 comprises a channel 122 disposed therethrough. The optic member 110 is placed through this channel 122 such that an anterior end 112 of the optic member 110 extends out of one side of the support 120 and a posterior end 114 of the optic member 110 extends out the opposite side of the support 120. The optic member 110 and support 120 may be secured together, such as with epoxy, cyanoacrylate, or other appropriate bonding and/or fusing material.

The biocompatible support 120 is further structured to be secured anterior to a cornea of a patient's eye and to engage soft tissue. Many of the keratoprostheses currently known "sandwich" the cornea between a back plate disposed posterior of the cornea and a forward plate on the anterior side of the cornea, or position the keratoprosthesis in an intralamellar arrangement, within the cornea such as in a supra-Descemet fashion, or behind/posterior to the cornea. Such placement is prone to inflammation, increased ocular pressure and extrusion of the prosthesis from epithelial ingrowth. In contrast, the present keratoprosthesis 100 is disposable entirely anterior to the cornea, as depicted in FIGS. 6 and 9a through 9c. Accordingly, negative effects on intraocular pressure are avoided, and as will be described in greater detail hereinafter, epithelial infiltration is significantly reduced. Moreover, although some known keratoprostheses incorporate titanium into portions of the keratoprosthesis, the use of titanium is small, and these earlier keratoprostheses are implanted within the cornea, leading to inflammation, increased ocular pressure, and extrusion as previously noted. Titanium has never been used before as a support or skirt of a keratoprosthesis that is positioned outside of or anterior to the cornea, as used herein.

Figure 3:
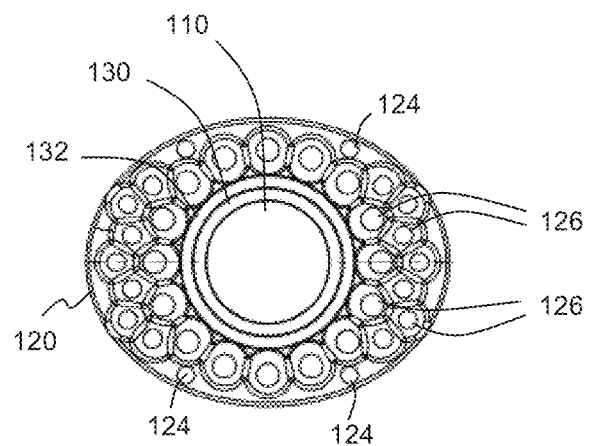
FIG. 3 is a top plan view of the keratoprosthesis of FIG. 1.
Figure 4A:
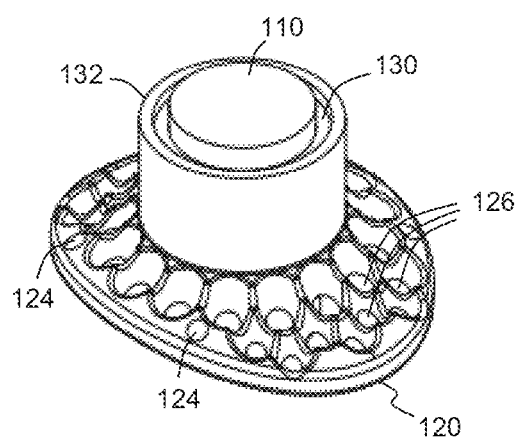
FIG. 4a is a perspective view the keratoprosthesis of FIG. 1.
Figure 6:
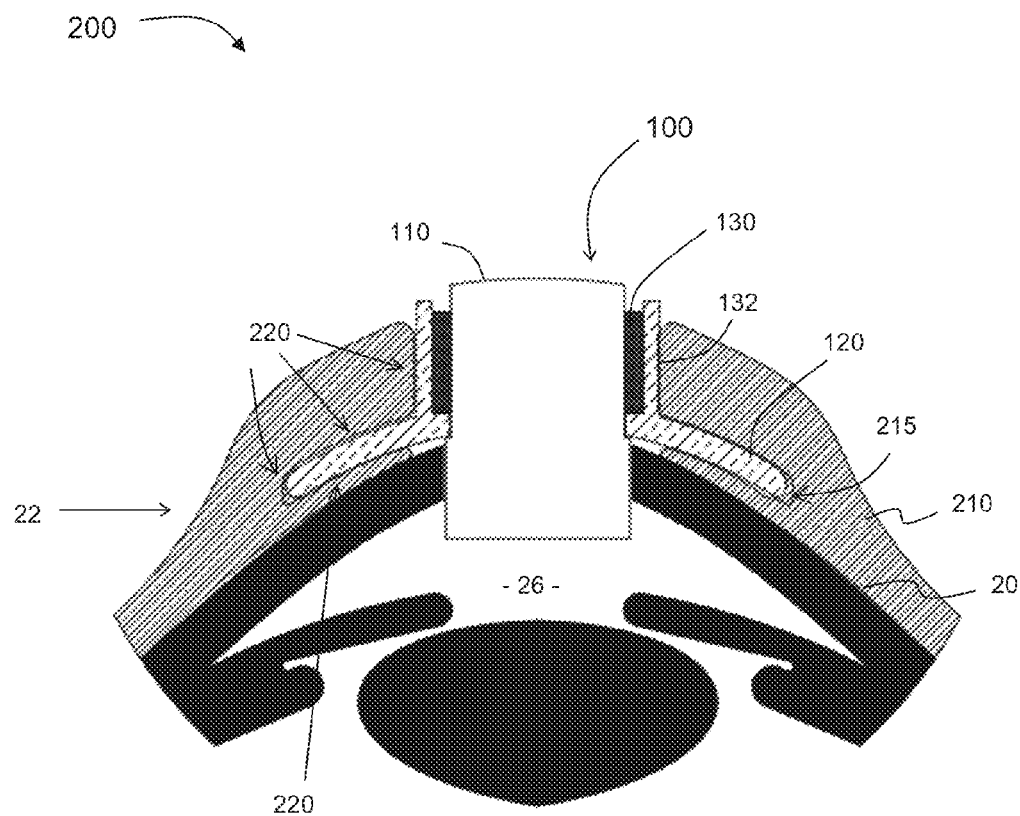
FIG. 6 is a cross-sectional view of one embodiment of the system of the present invention.

More specifically, as seen in FIG. 6, the support 120 is structured to engage a receiving area 215 of the isolated soft tissue 210, which is described in greater detail hereinafter with reference to the system 200 of the present invention. To facilitate attachment in at least one embodiment, as depicted in FIGS. 3 and 4, the support 120 comprises a plurality of apertures 124 disposed along the periphery of the support 120. In one example, the support 120 includes approximately four apertures 124 disposed at evenly spaced intervals along the periphery of the support 120, although other embodiments may include a different number of apertures 124. These apertures 124 are dimensioned and positioned to facilitate the attachment of the support 120 to the surrounding environment and secure the keratoprosthesis 100 in place upon implantation. For instance, in one embodiment each aperture 124 has a diameter of approximately 0.3 millimeters. The apertures 124 are preferably sized to permit sutures to pass therethrough such that the support 120 may be secured in place by suture fixation to the surrounding environment, such as the surrounding isolated soft tissue 210 and/or the cornea 20. The support 120 is further securable by adhesion of the soft tissue thereto, to be described in greater detail with regard to the system 200 of the present invention.

Figure 4B:
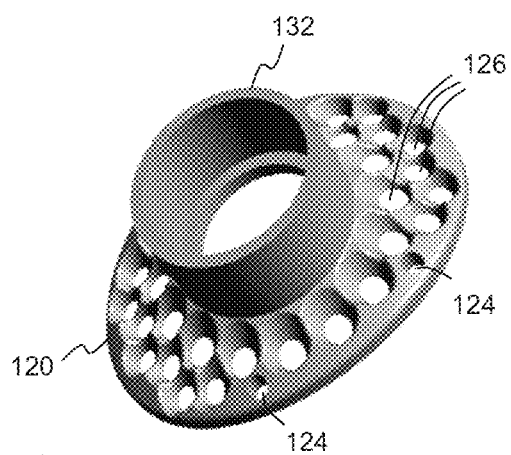
FIG. 4b is a perspective view of the support and collar of the keratoprosthesis of FIG. 1.
Figure 5A:
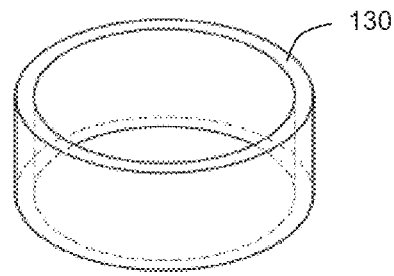
FIG. 5a is a perspective view of the locking member of FIG. 1.
Figure 5B:
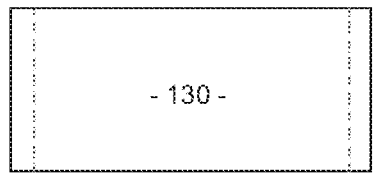
FIG. 5b a side elevation view of the locking member of FIG. 1.
Figure 5C:
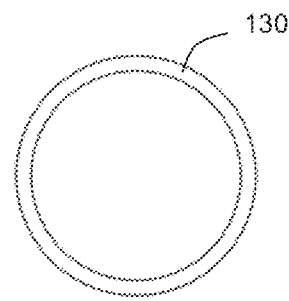
FIG. 5c a top plan view of the locking member of FIG. 1.

The size and dimension of the support 120 may vary as previously described, but is contemplated to be large enough to permit securing of the keratoprosthesis 100 and to enable soft tissue adhesion, and yet may be small enough to permit the free transfer of nutrients through the cornea. For example, the diameter of a typical cornea is between approximately 9.5 to 13 millimeters horizontally and approximately 9.21 and 12.4 millimeters vertically. A preferred embodiment of the support 120 will therefore measure a smaller diameter than the cornea to allow for perfusion of nutrients through the uncovered cornea extending around the circumference of the keratoprosthesis 100. If too large a surface of the cornea is covered, corneal melting may occur, which is detrimental to ocular health. To prevent this, in at least one embodiment, the support 120 may further comprise a plurality of openings 126, as best depicted in FIGS. 3 through 4*b*. These openings 126 are disposed throughout the support 120 to increase the surface area of the support 120, accelerate healing and reduce corneal melting. In some embodiments the openings 126 collectively give a mesh appearance to the support 120. For instance, in at least one embodiment each opening 126 measures approximately 0.15 to 0.4 millimeters in diameter. Since the openings 126 create spaces in the support 120, the openings 126 are therefore also disposed in nutrient transmitting relation to the cornea to allow the perfusion of nutrients through the corneal wall and maintain the proper corneal pressure. Moreover, the soft tissue 210 surrounding the implanted keratoprosthesis 100 may grow through the openings 126 of the support 120, thus providing additional stability to the keratoprosthesis 100. In at least one embodiment, the openings 126 have a contour, such as a concave shape or conical conformation from the superficial to the deep aspect of the support 120, as best shown in FIG. 4*b*. The vector of each opening will be set perpendicular to the tangent of the curved surface of support 120. The contour of the openings 126 increases the surface area of the support 120 such that greater soft tissue adhesion may occur. In addition, the vector of the opening 126 facilitates the fibrous ingrowth and bridging between the superficial and deep aspects of the transplanted isolated soft tissue 210, such as mucosa, thus accelerating and promoting healing while limiting extrusion.

Moreover, and as can be seen from FIG. 4*b*, the edges of support 120, openings 126 and apertures 124 are shaped so as to avoid sharp edges. Accordingly, sutures will not inadvertently be cut by the edges of the apertures 124, nor will the mucosa or other soft tissue be injured during implantation or during a vigorous massage applied to the keratoprosthesis 100, as can be the case when the patient cleans the outer optical surface.

At least a portion of the surface of the support 120 is a treated surface that is structured to promote the adhesion of soft tissue thereto. The treated surface may comprise a texture, such as having a plurality of pores and/or extrusions that provides sufficient "footholds" for the soft tissue to grip and grow onto, thereby adhering to the support 120 over time. For example, the treated surface may comprise a texture having a surface microstructure wherein each "foothold" ranges generally from about 0.5 to 2 microns in diameter, and the treated surface comprises a plurality of such "footholds" that collectively form a textured surface and/or contour.

Moreover, the treated surface may be the surface facing the anterior cornea upon implantation (the deep aspect), the opposite surface facing outward from the eye upon implantation (the superficial aspect), and/or both surfaces. In at least one embodiment, the treated surface comprises substantially all of an outer surface of the support 120. As used herein, "substantially all" means a majority of the surface of the support 120, which may include the entire outer surface or almost all of the outer surface, including one or both sides, and should not be construed in a limiting sense. Indeed, in at least one embodiment, every surface of the support 120 is treated to create a texture and structure to promote adhesion. However, the channel 122 of the support 120 need not have a treated surface, since the channel 122 only contacts the optic member 110 and locking member 130. It does not contact the soft tissue 210, even upon implantation of the keratoprosthesis 100, and therefore does not need to be treated to create a texture for adhesion.

The treated surface may be the result of any number or type of treatment that would create the appropriate porosity, texture and/or microstructure on the surface of the support 120 to provide enhanced soft tissue adhesion capabilities. Examples include, but are not limited to, at least one of sandblasting and acid etching, or both. For instance, the support 120 may be sandblasted with a large grit, such as in the range of about 0.25 to 0.5 micrometers, although other sized grits are also contemplated and may be used depending on the desired texture or porosity to be formed. The grit may be made of alumina or other appropriate material capable of cutting and/or shaping the support 120 upon rapid firing, scraping, grinding, or other method of forming texture. The support 120 may also be acid etched, such as using a mixture of hydrochloric acid (HCl) and sulfuric acid ($H_2SO_4$), although other acids and combinations thereof are also contemplated. Indeed, even a single acid may be used for etching. Any concentration, strength, and ratio of acids may be used for acid etching as will yield the desired textured surface outcome. The acid etching may comprise subjecting the surfaces of the support 120 to be treated to boiling acids, such as those identified previously. In one example, the surfaces of the support 120 are treated with acid in the range of about 125° C. to 130° C. for approximately 5 minutes. Other acid treatment times and conditions that also result in an appropriate microstructure texture for soft tissue adhesion are also contemplated and within the spirit of the present invention.

In at least one embodiment, the keratoprosthesis 100 of the present invention also includes a collar 132 extending away from the support 120 and in at least partially encircling relation to the optic member 110, as best seen in FIGS. 1 and 6. Since the collar 132 is disposed in contacting relation with soft tissue upon implantation of the keratoprosthesis 100, it provides additional surface area for soft tissue adhesion. Accordingly, in a preferred embodiment, the collar 132 is made of a metal similar to that of the support 120, such as titanium, and may be milled or formed from the same piece of metal as the support 120 in appropriate embodiments. The collar 132 may be approximately 0.1 to 0.3 millimeters in thickness and have a height sufficient to extend from the support 120 to at least the edge of the soft tissue, or even through the soft tissue. For example, in one embodiment, the collar 132 extends approximately 3 millimeters from the anterior surface of the titanium skirt.

Moreover, in at least one embodiment the collar 132 comprises a treated surface having a textured structure to promote the adhesion of soft tissue thereto, similar to the support 120. The collar 132 may be treated by the same methods and protocols as the support 120 to accomplish such a textured structure, including but not limited to sandblasting and/or acid etching as previously described.

In at least one embodiment, the keratoprosthesis 100 further comprises a locking member 130, as best shown in FIGS. 1, 5A through 5C and 6. The locking member 130 is structured and disposed in interconnecting securing relation with the optic member 110 and support 120, and is disposed between the optic member 110 and the collar 132. Specifically, the locking member 130 connects and secures the optic member 110 to the support 120 and prevents the optic member 110 from sliding. In at least one embodiment, and as depicted in the various Figures, the locking member 130 is disposed in at least partially encircling relation to anterior side of the optic member 110, and so may be considered an annular ring, although configurations other than rings are also contemplated. The locking member 130 may be made of any appropriate material, such as PMMA, although other materials such as metals, including stainless steel or titanium, are possible. Further, the locking member 130 comprises a height sufficient to span the depth of an anterior portion of the soft tissue 210 in which the keratoprosthesis 100 is implanted, as shown in FIGS. 6 and 9a through 9c.

The locking member 130 may further be secured to the optic member 110, such as bonded, fused, or welded using appropriate materials. For instance, in embodiments in which the locking member 130 is made of PMMA, the solvent methyl ethyl ketone (MEK) may be applied to both the locking member 130 and the optic member 110, also comprised of PMMA, in order to fuse the two together. Of course, appropriate bonding agents may also be used, such as epoxy, cyanoacrylate, and others, particularly when the locking member 130 is made of a metal or other material. In still another embodiment, the locking member 130 comprises potting material, including but not limited to epoxy, liquid silicone (such as GE RTV 100 silicone rubbers), or other appropriate materials as may be of medical grade that can be used to fill in the space between the optic member 110 and collar 132.

Figure 7:
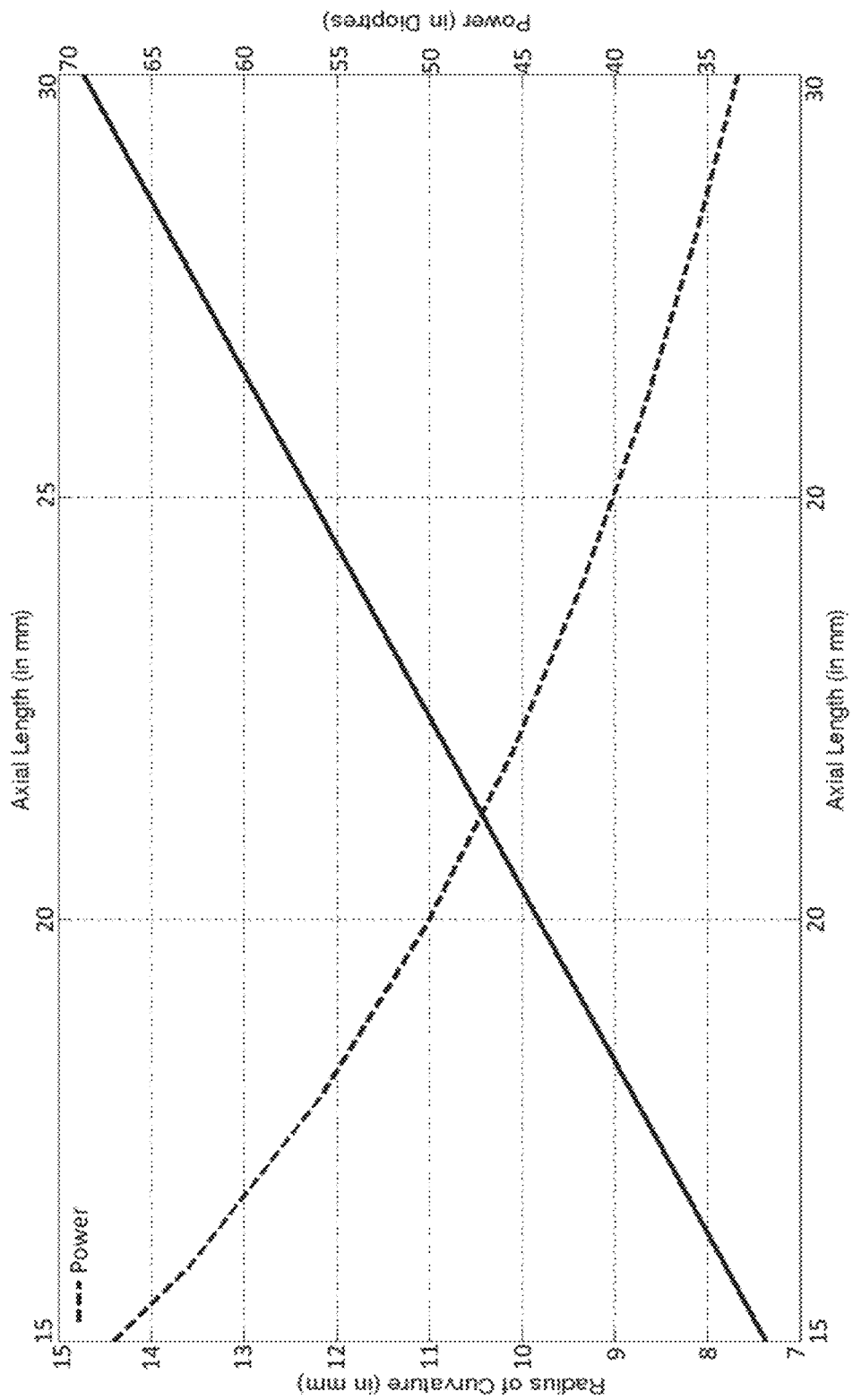
FIG. 7 is a graphical representation of the relationship of the radius of curvature and power in relation to the axial length of the keratoprosthesis.
Figure 8:
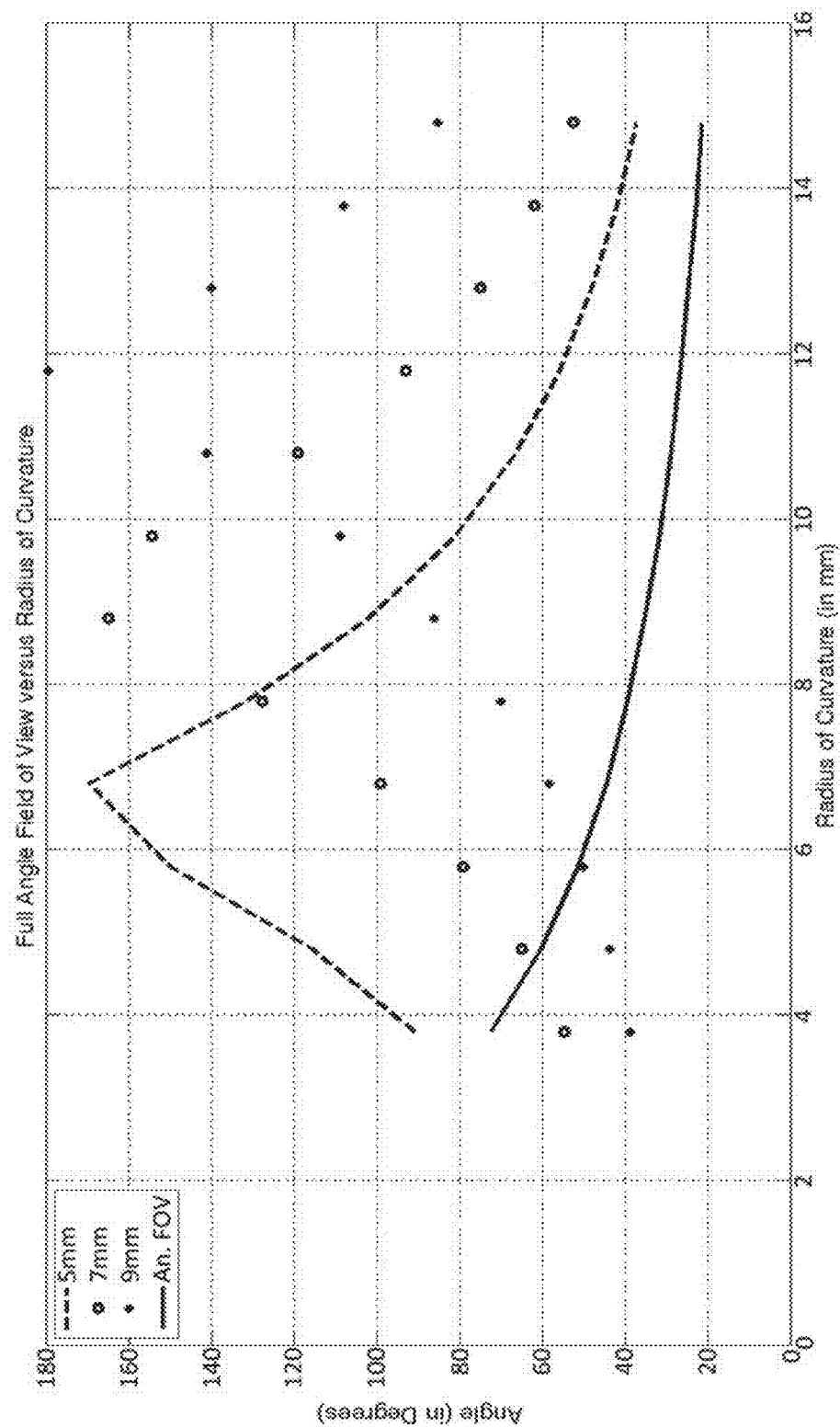
FIG. 8 is a graphical representation of the relationship of the angle field of view and radius of curvature of various embodiments of the keratoprosthesis of the present invention.

FIGS. 7 and 8 show some of the optical characteristics of the keratoprosthesis 100 of the present invention, including the field of view and radius of curvature for different sized keratoprostheses 100.

As previously mentioned, the present invention is also directed to a system 200 for corneal repair, as depicted schematically in FIGS. 6 and 9a through 9c. Generally, the system 200 comprises the keratoprosthesis 100 described above in conjunction with an isolated soft tissue segment 210 situated on the anterior surface 22 of a cornea 20.

Specifically, and with reference to FIG. 6, the isolated soft tissue segment 210 of the system 200 is any non-ocular tissue, such as oral buccal mucosa in one embodiment, although any other soft tissue that is capable of growing and adhering to surfaces upon transplantation may be used. The soft tissue segment 210 is isolated and/or extracted from a donor site where it naturally occurs. For example, in the case of oral mucosa, the isolated soft tissue 210 is taken from the cheek in the mouth. The donor site may be located on the patient receiving corneal repair, in which case the isolated soft tissue segment 210 is autologous and the risk of rejection is virtually eliminated. However, in other embodiments the donor site may be from a different individual, even from a different species, so long as the isolated soft tissue 210 will be able to grow and adhere to its surroundings upon transplantation of the graft without being rejected by the host. Ideally, the transplanted isolated soft tissue segment 210 will not cause a reaction in the host body, such as the mounting of an immune or inflammatory response. For this reason, autologous tissue transfers from the host are preferred, although the system 200 is not limited to such tissues.

The isolated soft tissue segment 210 is comparably sized to correspond to at least a damaged portion of cornea that is being repaired, up to and including the entire surface of the eye. Ultimately, the size of the isolated soft tissue segment 210 will be determined based on the size of the damaged cornea that is being repaired or replaced, and/or on the size of the eye. Therefore, in some embodiments, the isolated soft tissue segment 210 may measure up to the full size of the eye. On the other hand, the isolated soft tissue segment 210 may be minimally sized to repair even small areas of corneal damage.

The isolated soft tissue segment 210 of the present system 200 is disposable in covering relation to an exposed portion of the cornea 20 from which the damaged portion of the cornea has previously been removed. Accordingly, the isolated soft tissue segment 210 is positioned in direct contact with the exposed cornea 20. Therefore, the blood, oxygen, and other nutrients carried by the vascular network originating from the periphery of the host bed including the sclera and the insertions of the extraocular muscles, supply the isolated soft tissue segment 210 with the nutrients it needs to grow and adhere to its new environment on the corneal surface.

The system 200 further comprises a keratoprosthesis 100 as described previously, such as having a metal or titanium support 120. The keratoprosthesis 100 is disposed such that the optic member 110 is positioned in vision facilitating relation to the eye of the patient. For instance, as seen in FIGS. 6 and 9a through 9c, the optic member 110 of the keratoprosthesis 100 extends through the isolated soft tissue segment 210, through the cornea 20, and into the aqueous portion 26 of the eye.

Figure 9A:
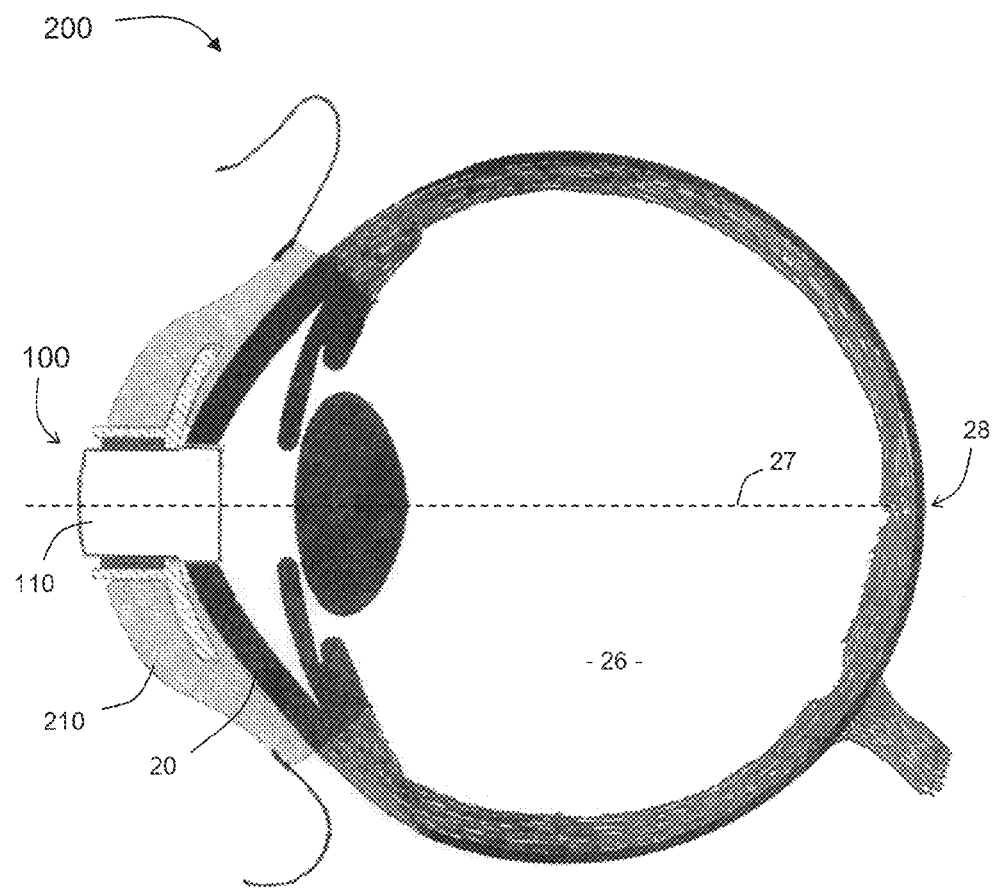
FIG. 9a is a schematic cross-sectional view of an eye with one embodiment of the system of the present invention, in which the lens and iris are intact.
Figure 9B:
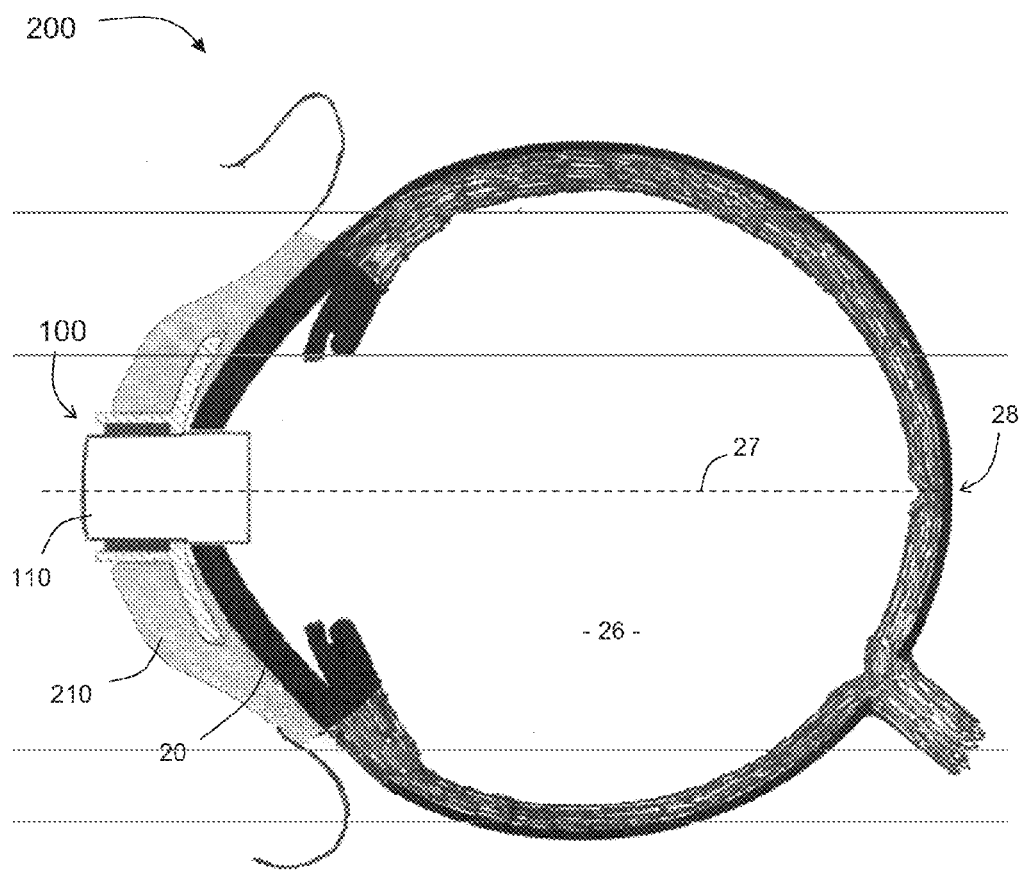
FIG. 9b is a schematic cross-sectional view of an eye with another embodiment of the system of the present invention, in which the lens and iris have been removed.

In some embodiments, such as depicted in FIG. 9b, the optic member 110 may have a longer cylinder which extends into the aqueous portion 26 of the eye. In such embodiments, it may be preferable to remove the crystalline lens of the eye and/or the iris in conjuction with using the present system 200 so as to avoid unwanted contact between the optic member 110 and lens and iris. In some embodiments, the lens and iris may need to be removed for other reasons, such as medical reasons, and so a longer optic member 110 may used.

Figure 9C:
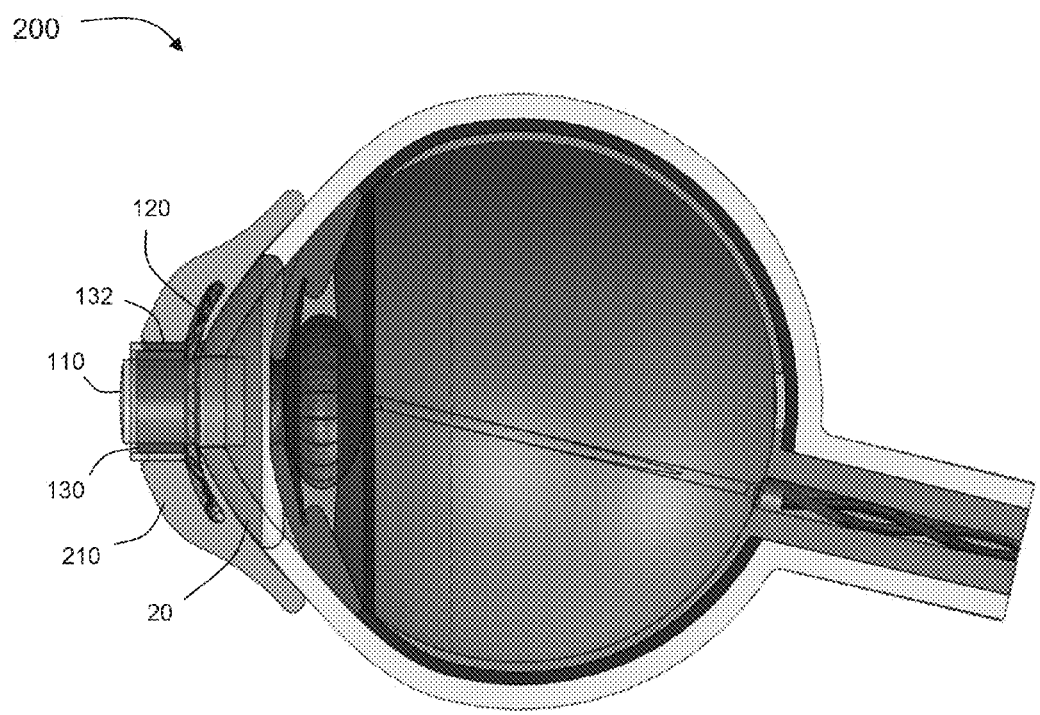
FIG. 9c is a partial cross-sectional view of an eye with the system of the present invention indicating the three-dimensional aspects of the invention.

In other embodiments, a shorter optic member 110 may be preferred. For instance, when the lens and/or iris remain intact within the eye, the use of a shorter optic member 110 may be necessary to avoid contacting the iris with the optic member 110, which causes irritation and inflammation. Similarly, a shorter optic member 110 avoids contact between the posterior surface of the optic member 110 and the lens upon the application of pressure to the eye, such as during massage of the eye or washing the surface of the optic member 110, and so avoids contact that could lead to cataract formation. Also, a shorter optic member 110 provides a greater field of view, which may be desired for vision purposes. Accordingly, in some embodiments, the optic member 110 is sufficiently long to pass fully through the isolated soft tissue 210, and yet is also sufficiently short so as to avoid contact with the iris and lens, even upon external pressure. Accordingly, the keratoprosthesis 100 may be positioned such that the posterior surface of the optic member 110 is substantially coincident with the posterior surface of the cornea 20, as shown in FIG. 9a. Of course, the optic member 110 may be positioned so that it extends slightly into the aqueous portion 26 of the eye even when the iris and lens are present, as seen in FIGS. 6 and 9c, and may comprise some intermediate length cylinder to facilitate such placement. FIG. 9c also depicts a more three-dimensional rendering of one embodiment of the system 200 and keratoprosthesis 100.

Once placed, the keratoprosthesis 100 is secured in position as described above, such as by suturing through the various peripheral apertures 124 disposed in the support 120, so that the optic member 110 does not move or drift from position and can provide an accurate line of sight, depicted schematically as dotted line 27 in FIGS. 9a and 9b, from outside the eye to the retina 28 for vision.

In general, the keratoprosthesis 100 is structured to be disposed and secured in engaging relation with the isolated soft tissue segment 210 anterior to the cornea 20, and more in particular, anterior to the exposed portion of the cornea. Accordingly, the isolated soft tissue segment 210 is disposed in direct contacting relation with anterior surface 22 of the exposed cornea 20, and the keratoprosthesis 100 is disposed in contacting relation to the isolated soft tissue segment 210. In at least one embodiment, the keratoprosthesis 100 is disposed within the isolated soft tissue segment 210. Moreover, the support 120 of the keratoprosthesis 100 is positioned in spaced relation, or substantially isolated relation, from the anterior 22 of the exposed portion of cornea 20. In other words, the support 120 of the keratoprosthesis 100 does not directly touch the cornea 20, but rather is positioned anterior to the cornea. Instead, the support 120 of the keratoprosthesis 100 contacts only the isolated soft tissue segment 210.

Such positioning is advantageous since the keratoprosthesis 100 is structured to facilitate the adhesion of the isolated soft tissue 210 surrounding it in the present system 200 to the keratoprosthesis 100. As described above, the keratoprosthesis 100 has certain characteristics, such as a metal and/or titanium support 120 and a treated surface(s) providing certain textures to promote the adhesion of soft tissue thereto. Accordingly, when positioned within the isolated soft tissue segment 210 of the present system 200, the keratoprosthesis 100 is structured to promote the formation of a bioseal 220 between the isolated soft tissue segment 210 and the keratoprosthesis 100, as indicated in FIG. 6. The bioseal 220 forms a mechanical seal at the interface where the isolated soft tissue segment 210 contacts and adheres to the surfaces of the keratoprosthesis 100, including the surfaces of the support 120 as well as the collar 132 that extends through the isolated soft tissue segment 210. Moreover, due to the nature of the isolated soft tissue segment 210 and the characteristics of the keraoprosthesis 100, soft tissue adhesion forming the bioseal 220 occurs faster than the peripheral corneal epithelium can grow into the same space. Therefore, the bioseal 220 prevents epithelial infiltration and bacterial invasion resulting in infections, and therefore also prevents extrusion of the keratoprosthesis 100. The end result is a more successfully integrated keratoprosthesis 100, and better prognosis for corneal repair.

Figure 10:
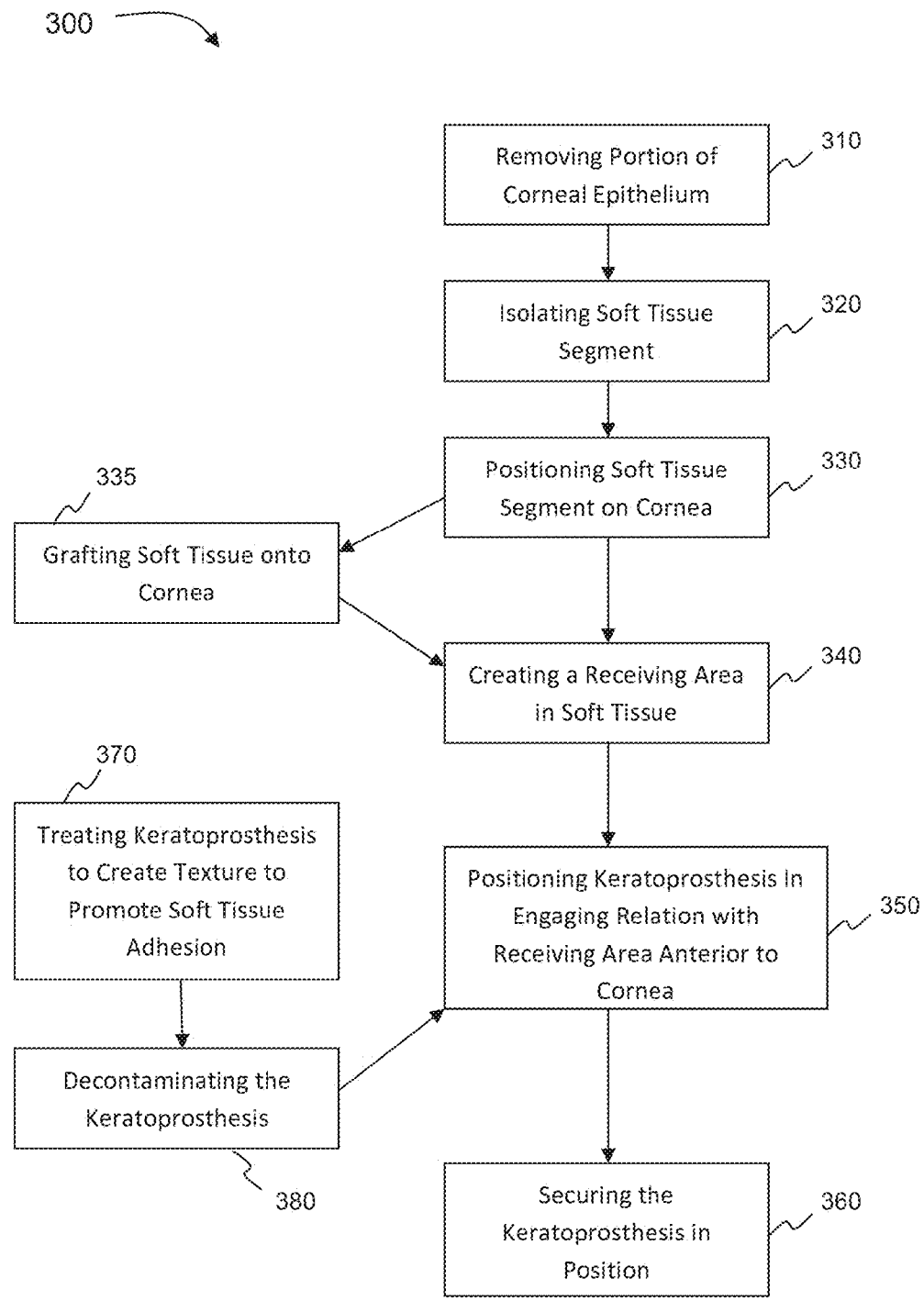
FIG. 10 is a schematic diagram of one embodiment of the method of the present invention.

The present invention is further directed to a method of corneal repair by implanting a keratoprosthesis, as at 300 and depicted schematically in FIG. 10. Specifically, the method 300 includes preparing the eye, which involves at least removing a portion of corneal epithelium from an eye of the patient so as to define a de-epithelialized section of cornea, as at 310. This portion of removed corneal epithelium corresponds to at least a portion of, or all or substantially all of the damaged cornea. Moreover, the corneal epithelium may be taken from any portion of the cornea, but in at least one embodiment is taken from the superficial aspect of the cornea.

The method further includes isolating a segment of soft tissue, as at 320. As previously described, such soft tissue may be isolated from any appropriate non-ocular tissue site, such as buccal mucosa of the oral cheek, and is sized to substantially correspond to at least the de-epithelialized section of the cornea, or to be larger than the de-epithelialized section of the cornea, up to and including the size of the entire eye. The soft tissue may be isolated from a donor site on the patient or other donor tissue as described above.

Once isolated, the method 300 further comprises positioning the isolated soft tissue segment on the de-epithelialized section of cornea, as at 330. More specifically, and as explained previously with reference to the system 200, the isolated soft tissue segment is overlaid on the de-epithelialized section of cornea, in contacting relation with the cornea and the circumferential vascular network of the peripheral recipient site to provide needed nutrients for transplanted soft tissue to grow and graft thereto. In at least one embodiment, the method 300 also comprises grafting the transplanted and positioned isolated soft tissue segment to the cornea, as at 335. In one example, the transplanted soft tissue is permitted to grow and the eye allowed to heal for approximately one month, although other lengths of time are also permitted. In such embodiment, the entire method 300 may be performed in a single procedure, rather than the multi-step procedure currently required by other methods.

The method 300 further includes creating a receiving area in the transplanted soft tissue segment, as at 340. Such receiving area is sized to accommodate a keratoprosthesis therein, such as the keratoprosthesis 100 described above. In at least one embodiment, creating a receiving area 340 includes creating an incision in the transplanted soft tissue, so as to form a flap, pocket, or other similar structure. The receiving area may be created at any depth within the soft tissue, such as for example ⅔ to ¾ of the way deep into the soft tissue, but preferably does not disrupt the contact of the soft tissue with the underlying cornea. The receiving area is therefore also created anterior to the cornea.

Continuing with FIG. 10, the method 300 further comprises positioning a keratoprosthesis in engaging relation with the receiving area of the soft tissue segment, as at 350. As noted previously, the keratoprosthesis is inserted and positioned so as to be anterior to the cornea and in vision facilitating relation to the eye of the patient. In at least one embodiment, inserting the keratoprosthesis is accomplished in a manner that substantially isolates the support of the keratoprosthesis from direct contact with the de-epithelialized section of cornea, as described previously. Moreover, in at least one embodiment, the keratoprosthesis is positioned within the receiving area of the isolated soft tissue, such as within a pocket created in the isolated soft tissue. In other embodiments, the keratoprosthesis is inserted so as to be at least partially surrounded by isolated soft tissue. Indeed, the keratoprosthesis may be inserted so as to be entirely surrounded by isolated soft tissue.

The method 300 further includes securing the keratoprosthesis in position, as at 360. Securing the keratoprosthesis prevents it from drifting in the receiving area. A stationary position allows the soft tissue to be able to adhere to the keratoprosthesis over time. Moreover, securing the keratoprosthesis maintains the position of the optic member, and therefore permits prolonged accurate vision using the keratoprosthesis. In at least one embodiment, securing 360 involves suturing the keratoprosthesis to at least a portion of the surrounding environment, such as to the surrounding soft tissue, cornea, anterior cornea, conjunctiva of the eye, etc. Such suturing may be accomplished through the apertures located along the periphery of the support of the keratoprosthesis, as described previously. In other embodiments, the keratoprosthesis may be secured to the surrounding environment, including the surrounding soft tissue, anterior cornea, conjunctiva, etc. by methods other than suturing.

In at least one embodiment, the present method 300 further comprises treating at least a portion of an exterior surface of the keratoprosthesis, as at 370, to create a treated surface having a textured contour that promotes the adhesion of soft tissue thereto. At least the surfaces that will contact soft tissue upon implantation are treated 370. In some embodiments, the entirety of every exterior surface of the keratoprosthesis is so treated to create a textured surface. For example, treating 370 may comprise treating one or both sides of the support of the keratoprosthesis, and may further comprise treating the outer surface of the collar 132. Moreover, treating 370 may occur by sandblasting and/or acid etching the surfaces of the keratoprosthesis, as previously described, and may occur by additional methods that produce a sufficient texture on the surface for promoting the adhesion of soft tissue. Such treating 370 preferably occurs prior to implantation of the keratoprosthesis 100.

In at least one embodiment, the method 300 further comprises decontaminating or sterilizing the treated keratoprosthesis, as at 380. For instance, at least the portion of the keratoprosthesis that has been treated 370 is decontaminated 380, including the surfaces of the support and collar. Such decontamination or sterilization 380, which terms may be used interchangeably, involves any appropriate method of cleaning and eliminating the surfaces of particulates, microorganisms such as bacteria, viruses, mold, fungus, and other foreign matter that may be detrimental to successful implantation. For example, decontamination 380 may occur according to the guidelines and protocol set forth in ASTM b600-11. In some embodiments, the entire keratoprosthesis is decontaminated 380, such as prior to implantation, to reduce the chance of infection and complications.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

The invention claimed is:

1. A keratoprosthesis comprising:
   an optic member disposable in vision facilitating relation to an eye of a patient;
   a biocompatible support having a channel disposed through said support, the channel defining a collar extending away from an anterior side of said biocompatible support;
   said optic member disposed in said channel of said support such that the collar is disposed in at least partially surrounding relation to the optic member, said biocompatible support structured to be secured in place at a position anterior to a cornea of a patient's eye and to engage soft tissue;
   at least a portion of a surface of said biocompatible support including a treated surface structured to promote adhesion of soft tissue thereto, wherein said biocompatible support comprises a metallic material; and wherein said collar and said biocompatible support comprise the same metallic material.

2. The keratoprosthesis as recited in claim 1, wherein said biocompatible support comprises titanium.

3. The keratoprosthesis as recited in claim 2 wherein said biocompatible support is made entirely of titanium.

4. The keratoprosthesis as recited in claim 2 wherein said biocompatible support comprises a core of at least one type of biocompatible material and at least one outer surface comprising titanium.

5. The keratoprosthesis as recited in claim 1 wherein said biocompatible support is disposable and securable in spaced relation to an anterior cornea.

6. The keratoprosthesis as recited in claim 1 wherein said biocompatible support is structured to engage a receiving area in soft tissue located anterior to the cornea.

7. The keratoprosthesis as recited in claim 1 wherein said biocompatible support comprises a diameter of approximately 10 millimeters.

8. The keratoprosthesis as recited in claim 1 wherein said biocompatible support comprises an elliptical shape.

9. The keratoprosthesis as recited in claim 1 wherein said biocompatible support comprises a plurality of apertures disposed along a periphery thereof to facilitate attachment of said biocompatible support.

10. The keratoprosthesis as recited in claim 9 wherein each of said plurality of apertures comprises a diameter of approximately 0.3 millimeters.

11. The keratoprosthesis as recited in claim 1 wherein said biocompatible support comprises a plurality of openings disposed throughout said biocompatible support in nutrient transmitting relation to the cornea.

12. The keratoprosthesis as recited in claim 11 wherein at least one of said plurality of openings comprise a contour to increase the surface area of said biocompatible support.

13. The keratoprosthesis as recited in claim 12 wherein at least one of said plurality of openings comprises a concave contour.

14. The keratoprosthesis as recited in claim 13 wherein at least one of said plurality of openings comprises a conical configuration.

15. The keratoprosthesis as recited in claim 1 wherein substantially all of an outer surface of said biocompatible support comprises a treated surface structured to promote adhesion of soft tissue thereto.

16. The keratoprosthesis as recited in claim 1 wherein said treated surface of said biocompatible support comprises a texture having microstructures ranging from generally about 0.5 to 2 microns in diameter.

17. The keratoprosthesis as recited in claim 1 wherein said surface is treated with at least one of sandblasting and acid etching to create enhanced soft tissue adhesion capabilities.

18. The keratoprosthesis as recited in claim 1 further comprising the collar disposed fully surrounding an outer wall of said optic member.

19. The keratoprosthesis as recited in claim 1 wherein said collar comprises at least one treated surface structured to promote adhesion of soft tissue thereto.

20. The keratoprosthesis as recited in claim 19 wherein said at least one treated surface of said collar comprises a texture having microstructures ranging from generally about 0.5 to 2 microns in diameter.

21. The keratoprosthesis as recited in claim 20 wherein said collar is treated with at least one of sandblasting and acid etching to create said texture of said at least one treated surface.

22. The keratoprosthesis as recited in claim 1 wherein said collar comprises a height of approximately 3 millimeters.

23. The keratoprosthesis as recited in claim 1 wherein said optic member comprises polymethylmethacrylate (PMMA).

24. The keratoprosthesis as recited in claim 1 wherein said optic member is secured within said channel of said biocompatible support.

25. The keratoprosthesis as recited in claim 1 further comprising a locking member structured and disposed in interconnecting securing relation between said optic member and said support.

26. The keratoprosthesis as recited in claim 25 wherein said locking member is disposed in at least partially encircling relation to said optic member.

27. The keratoprosthesis as recited in claim 26 wherein said locking member is disposed between said optic member and the collar extending from an anterior side of said biocompatible support.

28. The keratoprosthesis as recited in claim 25 wherein said locking member is secured to said optic member with methylethylketone (MEK).

29. The keratoprosthesis as recited in claim 25 wherein said locking member comprises polymethylmethacrylate (PMMA).

* * * * *

UNITED STATES PATENT AND TRADEMARK OFFICE
CERTIFICATE OF CORRECTION

PATENT NO. : 9,974,646 B2
APPLICATION NO. : 14/426195
DATED : May 22, 2018
INVENTOR(S) : Jean-Marie Parel et al.

Page 1 of 1

It is certified that error appears in the above-identified patent and that said Letters Patent is hereby corrected as shown below:

On the Title Page

In Column 1, under item (*) "Notice", Line 3, "0 days. days." should read -- 0 days. --.

Item (60), Line 1, "60/696,937," should read -- 61/696,937, --.

In the Specification

Column 1, Lines 10-11, "60/696,937" should read -- 61/696,937 --.

Signed and Sealed this
Sixteenth Day of October, 2018

Andrei Iancu
*Director of the United States Patent and Trademark Office*